United States Patent [19]

Bernat et al.

[11] Patent Number: 4,791,102
[45] Date of Patent: Dec. 13, 1988

[54] DERIVATIVES OF THE N α-ARYLSULPHONYLAMINOACYL-P-AMIDINOPHENYLALANINAMIDES, THEIR PREPARATION PROCESS, THEIR USE AS MEDICAMENTS AND THE PHARMACEUTICAL COMPOSITIONS CONTAINING THEM

[75] Inventors: André Bernat, Ugnaux; Denis Delebassee, Portet; Daniel Frehel, Toulouse; Jean-Pierre Maffrand, Portet; Eric Vallee, Tournefeuille, all of France

[73] Assignee: Sanofi, France

[21] Appl. No.: 6,421

[22] Filed: Jan. 23, 1987

[30] Foreign Application Priority Data

Jan. 24, 1986 [FR] France .................. 86 01399
Jan. 24, 1986 [FR] France .................. 86 01400

[51] Int. Cl.⁴ .................. A61K 37/02; C07C 143/78; C07D 279/10; C07D 265/30; C07D 241/04; C07D 207/00; C07D 211/06

[52] U.S. Cl. .................. 514/19; 564/84; 564/91; 544/391; 544/168; 544/58.4; 548/540; 546/226

[58] Field of Search .................. 514/19; 564/84, 91; 544/391, 168, 58.4; 548/540; 546/226

[56] References Cited

FOREIGN PATENT DOCUMENTS 155954 7/1981 German Democratic Rep. .

OTHER PUBLICATIONS

Chem. Abstr. vol. 97 (1982) 105943.
Chem. Abstr. vol. 99 (1983) 99022.
Chem. Abstr. vol. 100 (1984) 29426.
Chem. Abstr. vol. 102 (1985) 145184.
Chem. Abstr. vol. 101 (1984) 211666.
Chem. Abstr. vol. 101 (1984) 86232.
Chemical Abstracts, vol. 98, 1983, p. 645, No. 107770 b, Wagner, Guenther et al.
French Search Report for Application, 86 01 399.
French Search Report for Application 86 01 400.
Chemical Abstracts, vol. 99, 1983, p. 279, No. 18600z, J. Stuerzebecher et al.
Chemical Abstracts, vol. 102, 1985, p. 229, No. 91802b, U. Griessbach et al.

Chemical Abstracts, vol. 104, 1986, p. 43, No. 475z, J. Hauptmann et al.
Chemical Abstracts, vol. 104, 1986, p. 31, No. 45508d, B. Kasier et al.

Primary Examiner—Delbert R. Phillips
Attorney, Agent, or Firm—Wegner & Bretschneider

[57] ABSTRACT

The present invention is concerned with compounds with the formula:

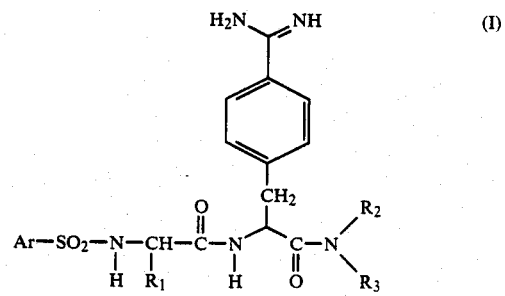

in which:
$R_1$ represents a lower alkyl, a lower hydroxy alkyl or a benzyl group, a phenyl group or a 4-hydroxy phenyl group:
$R_2$ and $R_3$, identical or different, each represents a lower alkyl or hydroxyalkyl, lower alkenyl, or lower alkynyl radical, or together with the nitrogen to which they are attached, they form a saturated heterocycle such as morpholino, thiomorpholino, pyrrolidino unsubstituted or substituted by an alkoxycarbonyl or carboxyl group, piperazino, 4-(lower alkyl)-piperazino, 4-(lower hydroxyalkyl)-piperazino, or piperidino unsubstituted or substituted by a lower alkyl, benzyl, hydroxy, lower hydroxyalkyl, amino, lower aminoalkyl, alkoxycarbonyl or carboxyl group,
Ar represents a phenyl, an alpha-naphthyl or a possibly substituted beta-naphthyl group, or a possibly substituted heteroaryl group chosen from pyridyl, quinolinyl, and isoquinolinyl, as well as their stereoisomers and their mixtures and their salts with pharmaceutically acceptable mineral or organic acids.

The invention is also concerned with a preparation process for the products with the formula (I), their use as medicaments and the intermediates for their synthesis.

11 Claims, No Drawings

DERIVATIVES OF THE N α-ARYLSULPHONYLAMINOACYL-P-AMIDINO-PHENYLALANINAMIDES, THEIR PREPARATION PROCESS, THEIR USE AS MEDICAMENTS AND THE PHARMACEUTICAL COMPOSITIONS CONTAINING THEM

The present invention is concerned with new derivatives of Nα-arylsulphonylaminoacyl-p-amidino-phenylalaninamides, their preparation process and their use as selective inhibiting agents of thrombin and antithrombotics.

The compounds of the invention answer to the general formula (I)

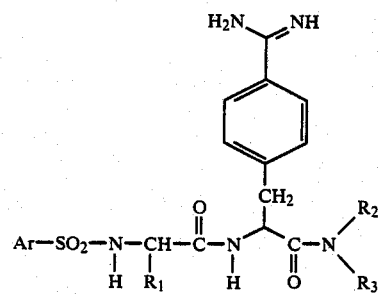

in which:

$R_1$ represents a lower alkyl, lower hydroxyalkyl, or benzyl group, a phenyl or a 4-hydroxyphenyl group.

$R_2$ and $R_3$, identical or different, each represents a lower alkyl or hydroxyalkyl, lower alkenyl or lower alkynyl radical, or they form together with the nitrogen to which they are attached, a saturated heterocycle such as morpholino, thiomorpholino, pyrrolidino unsubstituted or substituted by an alkoxycarbonyl or carboxyl group, piperazino, 4-(lower alkyl)-piperazino or piperidino unsubstituted or substituted by a lower alkyl, benzyl, hydroxy, lower hydroxyalkyl, amino, lower aminoalkyl, alkoxycarbonyl or carboxyl group.

Ar represents a phenyl, a possibly substituted alpha-naphthyl or beta-naphthyl group, or else a heteroaryl group chosen from pyridyl, quinolinyl, isoquinolinyl, possibly substituted. The preferred compounds with the above formula (I) are those in which $R_1$ represents an alkyl or hydroxyalkyl radical, those in which the group

represents a piperidino radical, substituted or not, and those in which Ar represents a naphthyl radical, substituted or unsubstituted. The carbon carrying the group $R_1$ can have R or S or RS configuration. All the compounds presenting the said configurations are included in the present invention. The compounds with the above formula (I) including one or more asymmetric centres can exist in the form of several isomers (diastereoisomers, enantiomers) and crystallization can bring in an enrichment of certain of the diastereo-isomers. The invention is concerned equally with each stereo-isomer and with their mixtures. The invention is concerned also with the addition salts of the compounds with the formula (I) with pharmaceutically acceptable mineral or organic acids. The terms "lower alkyl", "lower alkenyl" and "lower alkynyl" as used here, designate the radicals of branched or linear aliphatic hydrocarbon radicals containing up to six carbon atoms, such as methyl, ethyl, isopropyl, isobutyl, tertbutyl, n-hexyl, allyl, propargyl, crotyl, 2-methyl crotyl, 2-methyl allyl, 2-butyryl. Synthetic inhibitors of thrombin, having an amidino-phenylalanine group have been described in the literature. G. WAGNER and his collaborators (GD Pat. No. 142804 (16.07.80)) have described the compounds with the general formula (A):

The insertion of a glycine amino-acid residue between the sulphonyl group and the nitrogen N- of the p-amidinophenylalanine led to the compounds with the general formula (B), of which the activity in vitro is enhanced in comparison with those with the general formula (A) (G. WAGNER et Coll, GD Pat. No. 155954 (03.02.81)):

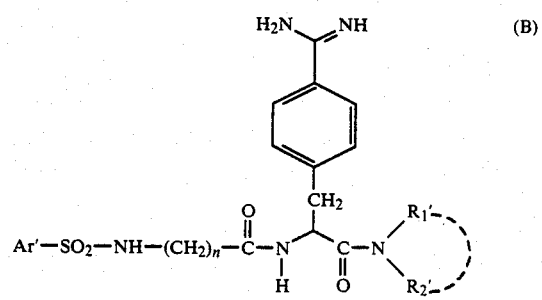

and, among the latter, the compound with the formula (B) where n=1, Ar'=beta-naphthyl, $NR'_1R'_2$=piperidino, hereafter designated compound (C) offers the best thrombin inhibiting activity in vitro (J. STURZEBECHER et al, Thrombosis Research 1983, 29, 635) and ex-vivo (J. HAUPTMANN et al, Thrombosis Research 1985, 39, 771). The products with the formulae (A) and (B) above are prepared according to the processes described in the patents GDR No. 142804 and GDR No. 155954, the amides are prepared starting from the corresponding free acids by activation and reaction with the corresponding amine. These processes imply reaction conditions which induce racemisations at the asymmetric centre. Furthermore, they do not permit compounds to be obtained carrying the substituent $R_1$.

The Applicant has found that the compounds with the formula (I) above can be obtained by a process which, by the use of carefully chosen coupling processes and protector groups, enables the asymmetric centres to be respected in their original configuration and does not induce racemisation.

This result, obtained, in contrast to the processes described by G. WAGNER and his collaborators, by first constructing the amide part

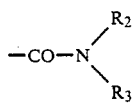

starting from the acid function of the synthon p-cyanophenylalanine, before the arylsulphonylaminoacyl part. The invention also has as its subject a preparation process for the compounds with the formula (I), characterized in that on the 4-cyanophenylalaninamide with the formula (II):

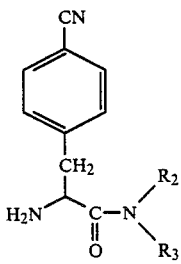

in which $R_2$ and $R_3$ have the same significances as in the formula (I), an acid with the formula

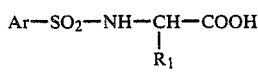

in its activated form (IV)

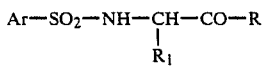

in which Ar and $R_1$ have the same significances as in the formula (I) and R represents a good nucleofuge group, such as chloro, alkoxycarbonyloxy or heteroaryl, is made to react, so as to obtain the compound with the formula (V)

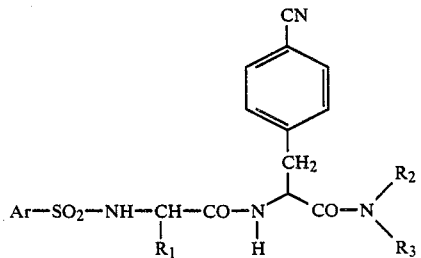

in which Ar, $R_1$, $R_2$ and $R_3$ have the same significances as in formula (I), which is treated with an excess of a saturated solution of hydrogen chloride gas in an alcohol with the formula X—OH in which X represents a lower alkyl radical, so as to obtain the compound with the formula (VI) in the hydrochloride form:

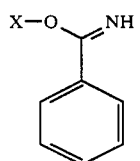

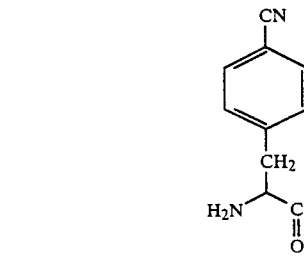

in which Ar, $R_1$, $R_2$, $R_3$ and X have the same significances as those already stated.

The imido-ester of formula (VI) is then treated with an excess of an ammonia gas solution in a lower alcohol at the boiling temperature of the reactional mixture in order to obtain the compound sought with the formula (I). This compound is isolated in the form of a salt, it being possible to obtain the free base by standard processes and to convert it into another pharmaceutically acceptable salt such as, for example, in addition to the hydrochloride, hydrobromide, sulphate, methanesulphonate, acetate, 2-naphthalene-sulphonate, maleate, fumarate, citrate, gluconate, dobesilate or sultosilate.

The preparation of the new compound with the formula (II) will be described below and is carried out starting with the 4-cyanophenylalanine with the formula:

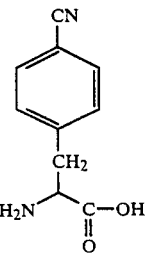

The acid with the formula

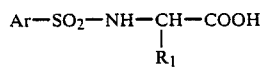

has been prepared by the following reactional scheme:

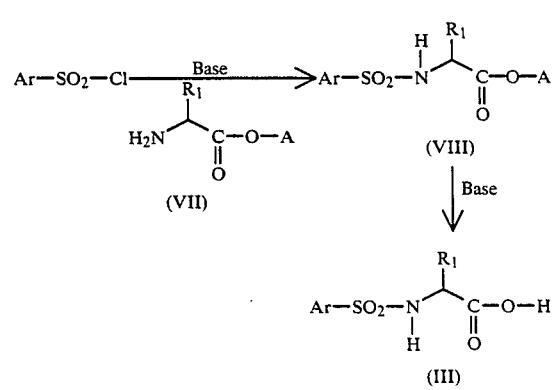

The introduction of an asymmetric centre in the amino-ester (VII: A=lower alkyl) of which the initial "R" or "S" configuration has to be preserved until the acid (III), requires the use of non-racemising methods.

the sulphonylation of the amino-ester (VII) takes place in a bi-phase medium, preferably a water/dichloromethane, water/chloroform, or water/carbontetrachloride mixture, in the presence of a base, preferably an alkaline carbonate such as the carbonate of potassium or of sodium, at temperatures between 10° C. and 25° C.

The saponification of the ester (VIII) takes place in a water/alcohol medium, such as water/methanol or water/ethanol, in the presence of an equivalent of an alkaline hydroxide, preferably sodium hydroxide, at temperatures between 10° C. and 25° C. The neutralization of the reactional medium by the addition of an equivalent of a 1N aqueous solution of a mineral acid, preferably hydrochloric acid, leads to the acid (III). This saponification can also be brought about in a water/organic medium, such as water/dioxan, in the same conditions. If it is not necessary to preserve the configuration of the asymmetric carbon, a standard method can be used. For the conversion of the acid with the formula (III) into an activated form with the formula (IV), two cases are to be considered:

(a) Case where the carbon carrying the group $R_1$ has the configuration "RS" (racemic): (non-stereo-specific synthesis).

The activation of the acid function can be done, for example, either by:

conversion of the acid function into an acyl halogenide (IV: R=Cl):

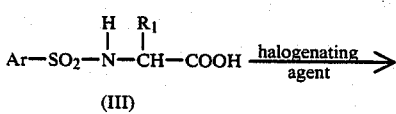

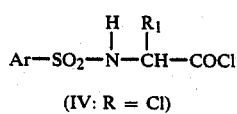

(IV: R = Cl)

according to the process described in the GDR Pat. No. 155954, or by:

conversion of the acid function into a mixed carbonic anhydride

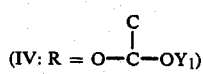

according to the reactional scheme:

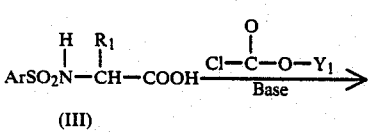

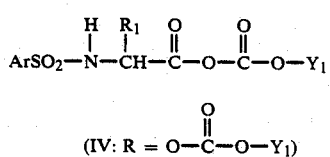

The reaction uses an alkyl chloroformate

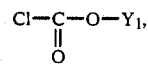

where $Y_1$ is a lower alkyl radical, branched or not, in the presence of a tertiary amine as base. The alkyl chloroformate preferentially used is ethyl chloroformate, ($Y_1=C_2H_5$) or isobutyl chloroformate, ($Y_1=CH_2-CH(CH_3)_2$).

The tertiary amine preferred is triethylamine. This condensation preferably takes place at temperatures between −5° C. and +10° C., in an inert solvent such as dichloromethane, chloroform or carbon tetrachloride.

The compounds obtained with the formula (IV) are made to react with the compounds with the formula (II) in an inert solvent, in the presence of an acid acceptor, such as a tertiary amine.

(b) Where the carbon carrying the group $R_1$ has the configuration "R" or "S" (enantiomers R or S) (Stereospecific synthesis).

In this case it is necessary to use processes which do not induce racemisation.

The conversion of the acid function of the compounds with the formula (III) into activated esters leads to compounds with the general formula (IV: R=O—Z) according to the reactional scheme:

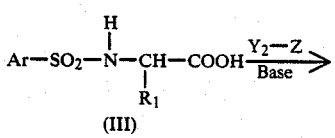

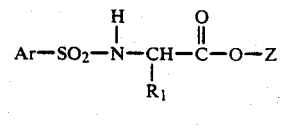

(IV: R = O—Z)

The coupling reagents $Y_2$—Z, which do not induce racemization, used for preference but which are not limitative, are the following:

1-hydroxybenzotriazole (HOBT)

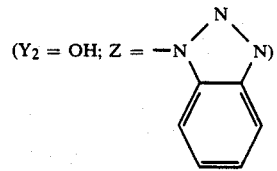

in the presence of N,N-dicyclohexylcarbodiimide (DCC) according to the method of operation described by E. C. JORGENSEN et al (J. Am. Chem. Soc. 1971, 93, 6318)

1-benzotriazolyloxy-tris(dimethylamino)phosphonium hexafluorophosphate (BOP)

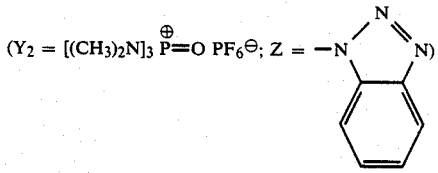

according to the operational method described by B. CASTRO et Coll. Synthesis 1976, 751.

N,N-bis(2-oxo-3-oxazolidinyl)phosphorodiamide chloride

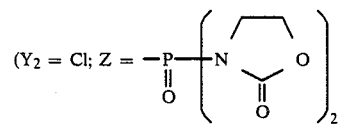

according to the operational method described by D. H. RICH et al (J. Am. Chem. Soc. 1985, 107, 4342.

The activation and coupling reaction takes place in the presence of tertiary amines, preferably triethylamine, in an inert solvent such as dichloromethane, dimethylformamide or acetonitrile, at temperatures between 15° C. and 40° C.

The formation of the imido-ester (VI) takes place in an alcohol medium such as methanol or ethanol, at a temperature between −10° C. and +10° C., preferably at 0° C., during a period of 16 to 24 hours.

The amidine of formula (I) is obtained by treating the compound (VI) previously obtained, without further purification, in an alcohol solution of ammonia gas at a normality of 3N to 15N, at ambient temperature, and the mixture is then heated to reflux for 1 to 3 hours.

The compounds with the formula (II) above, including one asymmetric center can exist in the form of two isomers (enantiomers). The invention is concerned with each stereoisomer as well as their mixtures. The invention is also concerned with their addition salts with mineral or organic acids.

The present invention is also concerned with a process for preparing the compounds with the formula (II), wherein an amino acid with the formula (IX) in its activated form (X):

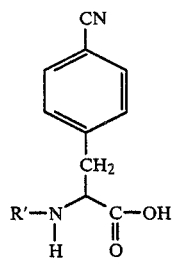 IX

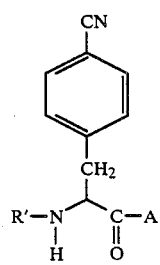 X in which R' represents an N-protecting group and A represents the moiety of a coupling reagent, are reacted with an amine having the formula (XI):

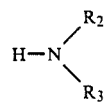 XI in which $R_2$ and $R_3$ are as in formula (II), in order to form a compound with the formula (XII):

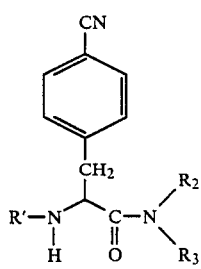 XII in which R', $R_2$ and $R_3$ have the same significances as in formulae (II) and (IX), and which, by cleavage of the protecting group R' gives the compounds of formula (II).

The formation of the compound with formula (IX) is obtained by fixing N-protecting group R' on p-cyanophenylalanine with the formula:

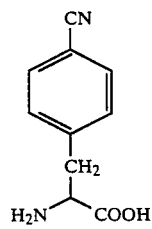

The N-protecting group, represented by R', is a group stable in alkaline medium used for the protection of the amino group of aminoacids in the peptide chemistry, for example the tert.butyloxycarbonyl group, preferably designed hereafter Boc; the 2-(3,5-dimethoxyphenyl) 2-propyl-oxycarbonyl group designed by Ddz; the 2-(4-biphenyl) 2-propyl-oxycarbonyl group designed by Bpoc; the (2-nitrophenyl)-sulphenyl group designed by Nps.

In order to obtain the activated acid with the formula (X) in which A represents the coupling reagent moiety, two cases are to be considered.

(a) Preparation process with conservation of the "R" or "S" configuration (stereo-specific synthesis)

In order to avoid inducing racemisation at the asymmetric center of the compound with the formula (XII) and to keep the initial configuration of the asymmetric center of the acid with the formula (IX), it is necessary to carry out the activation of the acid (IX) using the transformation of the acid into an activated ester (X) according to the reaction schema:

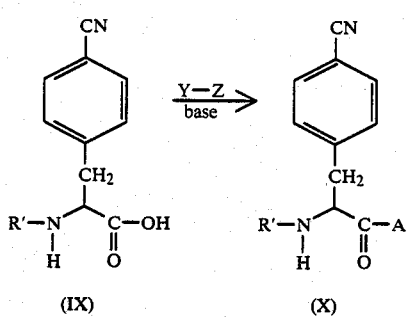 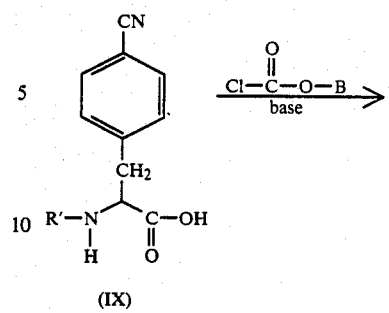

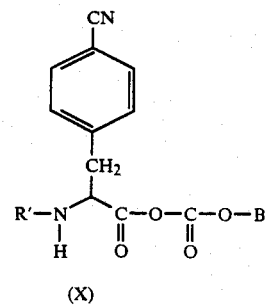

The coupling reagents Y—Z, which do not induce racemisation, preferably used, but not limitative, are the following:

1-Hydroxybenzotriazole (HOBT)

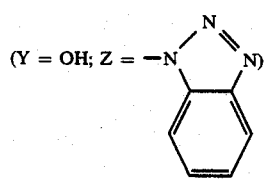

in the presence of N,N-dicyclohexylcarbodiimide (DCC) according to the method described by E. C. JORGENSEN et al. (J. Am. Chem. Soc. 1971, 93, 6318).

1-Benzotriazolyl-oxytris(dimethylamino)phosphonium hexafluorophosphate (BOP)

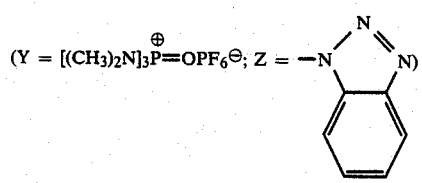

according to B. CASTRO et al. (Synthesis 1976, 751).

N,N-bis(2-oxo-3-oxazolidinyl)phosphorodiamide chloride

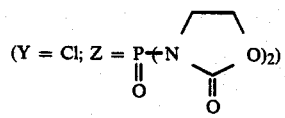

according to the method described by D. H. RICH et al. (J. Am. Chem. Soc. 1985, 107, 4342).

The activation and coupling reaction is carried out in the presence of tertiary amines, preferably triethylamine, in an inert solvent such as dichloromethane, dimethylformamide or acetonitrile, at temperatures comprised between 15° C. and 40° C.

(b) Preparation process without conservation of the configuration (non-stereo-synthesis)

The action of the acid function of the compound (IX) may be carried out by transformation of the acid function into a mixed anhydride (X: A=—O—CO—O—B) according to the reaction schema The reaction uses an alkyl chloroformate

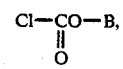

wherein B is a lower linear or non linear alkyl, in the presence of a tertiary amine as base. The alkyl chloroformate preferably used is ethyl (B=C$_2$H$_5$) or isobutyl (B=CH$_2$—CH(CH$_3$)$_2$) chloroformate. The preferred tertiary amine is triethylamine. This condensation is preferably carried out at temperatures comprised between −5° C. and +10° C., in an inert solvent such as dichloromethane, chloroform or carbon tetrachloride.

The starting product p-cyanophenylalamine was prepared according to one of the methods used in the literature (G. WAGNER et al. Pharmazie 1981, 36 (9), 597).

The compound with the formula (X) is reacted with the amine of formula (XI) in an inert solvent and in the presence of a tertiary amine.

The cleavage of the N-protecting group R' of the compound with the formula (XII) leads to Nα-substituted p-cyanophenylalamines with the formula (II). This cleavage is carried out in acidic medium, preferably a hydrobromic acid-acetic acid mixture or in trifluoroacetic acid (R'=Boc, Ddz, Bpox, Nps), in acetic acid (R'=Boc, Nps), in an ethyl acetate R'=Boc) solution saturated with hydrochloric gas, at temperatures comprised between 0° and 20° C.

EXAMPLE 1

Nα-(tertubyloxycarbonyl)p-cyanophenylalanine

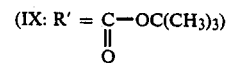

10 g (0.044 mole) of p-cyanophenylalamine and 88.2 ml (0.088 mole) aqueous 1N sodium hydroxyde are dissolved in 220 ml of dioxane. At ambient temperature and under an inert atmosphere, 1.77 g (0,044 mole) of magnesium and then 10.6 g (0.0484 mole) of diterbutyl dicarbonate are progressively added to the reaction medium. The medium is stirred at ambient temperature for 20 hrs. The crystals are filtered off and washed with water. The filtrate is evaporated and the residue is dissolved in water. The aqueous phase obtained is brought to pH=3 by adding a solution saturated with potassium hydrogenosulphate. The aqueous phase is extracted with 2×400 ml ethyl acetate, the organic extracts are dried on anhydrous sodium sulphate and evaporated to dryness. The crystals obtained are recrystallized in ethyl acetate or diisopropyl ether.

White crystals, yield: 88%, M.P.=147° C.

EXAMPLE 2

1-[Nα-(terbutyloxycarbonyl)p-cyanophenylalanyl]-piperidine

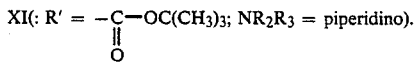

Activation of the acid function of the compound (IX: R=—C—OC(CH₃)₃) (example 1) into mixed anhydride

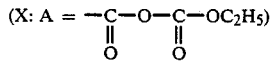

4.2 g (0.0416 mole) of triethylamine is added to a suspension of 11 g (0.0378 mole) of Nα-(terbutyloxycarbonyl)p-cyanophenylalanine (Ex. 1) in 125 ml dichloromethane, at 0° C., under an inert atmosphere. To the mixture which becomes homogeneous, a solution of 4.3 g (0.0395 mole) ethyl chloroformate in 10 ml dichloromethane is added dropwise. At the end of the addition, the reaction mixture is allowed to stand for 45 minutes at 0° C., then 3.4 g (0.0397 mole) piperidine dissolved in 10 ml dichloromethane is added dropwise at 0° C. The reaction mixture is allowed to return to ambient temperature and is left at this temperature for 15 hrs. The reaction medium is extracted with an aqueous solution saturated with sodium bicarbonate. The organic phase, after decantation, is dried on anhydrous sodium sulphate and evaporated to dryness. The oily residue, after trituration with diisopropyl ether, gives white crystals. These crystals are recrystallized in diisopropyl ether.

White crystals, yield: 81%, M.P. =132° C.

EXAMPLE 3

4-methyl 1-[Nα-(terbutyloxycarbonyl)p-cyanophenylalanyl]-piperidine

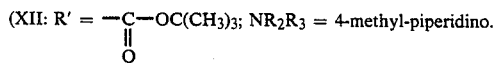

Activation by transformation of the acid function into the activated ester function, by using the non-racemising coupling reagent DCC/HOBT.

2.78 g (0.01 mole) of Nα-(tertbutyloxycarbonyl)p-cyanophenyl-alanine (Ex. 1) is dissolved in 50 ml of dichloromethane. Under an inert atmosphere, at ambient temperature, there are added successively 1 g (0.01 mole) of 4-methylpiperidine, 1.35 g (0.01 mole) of 1-hydroxy-benzotriazole (HOBT), 1.1 g (0.01 mole) of triethylamine. To the reaction medium there is added 2.06 g (0.01 mole) of N,N-dicyclohexylcarbodiimide (DCC) dissolved in 80 ml of dichloromethane at ambient temperature and the reaction medium is left for 15 hrs. at ambient temperature. The precipitate of dicyclohexylurea is filtered off and eliminated. The organic filtrate is washed with a saturated aqueous solution of sodium bicarbonate, and dried on anhydrous sodium sulphate. Evaporation gives a residue which is triturated with diisopropyl ether. The white crystals obtained are recrystallized in ethyl acetate.

White crystals, yield: 84%, M.P.=142° C. (ethyl acetate)

EXAMPLE 4

1-(p-cyanophenylalanyl)-piperidine (II: NR₂R₃=4-methylpiperidino)

4.1 g (0.0115 mole) of 1-[Nα-(terbutyloxycarbonyl)p-cyanophenylalanyl]piperidine (example 1) dissolved in 22 ml of ethyl acetate is added to 22 ml of a solution of ethyl acetate saturated with hydrochloric gas, cooled to 0° C. There is a progressive dissolution. The mixture is allowed to return to ambient temperature and left at ambient temperature for 15 hrs. The crystals precipitate, are filtered off, washed with ether and recrystallized in isopropanol.

White crystals, yield: 88%; M.P.=145° C. (hydrochloride).

EXAMPLE 5

1-(p-cyanophenylalanyl)-4-methyl-piperidine (II: NR₂R₃=4-methyl-piperidino)

Prepared according to the method described in Example 4, from 4-methyl 1-[Nα-(terbutyloxycarbonyl)p-cyanophenylalanyl]piperidine (Example 3).

White crystals, yield: 97%; M.P.=210° (isopropanol), hydrochloride.

EXAMPLE 6

1-[Nα-(Nα-betanaphthylsulphonyl-(R)-phenylalanyl)-p-cyanophenylalanyl]piperidine (V: Ar=betanaphthyl; R₁=CH₂—C₆H₅; NR₂R₃=piperidino)

To a suspension of 12.5 g (0.0245 mole) of 1-(p-cyanophenylalanyl)piperidine hydrochloride in 200 ml of dichloromethane there are added successively 15.1 g (0.0245 mole) of N-(betanaphthylsulphonyl)-(R)-phenylalanine, 4.3 g (0.0425 mole) of triethylamine, 6.5 g (0.0425 mole) of 1-hydroxybenzotriazole (HOBT). The reactional medium is cooled to between 0° C. and 5° C., then 8.8 g (0.0425 mole) of N,N-dicyclohexylcarbodiimide (DCC) dissolved in 50 ml of dichloromethane is added drop by drop. The reactional medium is left under good agitation at ambient temperature for 17 hours. The precipitate of dicyclohexylurea is filtered off, and the organic filtrate is washed with a saturated aqueous solution of sodium bicarbonate. The organic phase, dried on anhydrous sodium sulphate, is evaporated to dryness. The evaporation of the solvent leaves a residue which is triturated with ethyl acetate. The white crystals are filtered off and washed wih diisopropyl ether.

White crystals, yield: 64%, m.p.=173° C. (ethyl acetate).

Examples 7 to 12 use the same methods of operation as are described in example 6. They lead to the nitriles of formula (V) and result from the coupling of the synthons, with the general formula (II), with the acids with the general formula (III), previously activated by conversion of the acid function into an activated ester function (IV), using the non-racemising coupling reagent DCC/HOBT. They are summarized in the following table.

[Structure: naphthalene-SO$_2$-NH-CH(R$_1$)-C(=O)-NH-CH(CH$_2$-C$_6$H$_4$-CN)-C(=O)-NR$_2$R$_3$]

(V: Ar = betanaphthyl)

| Example | R$_1$ (configuration of the amino acid) | NR$_2$R$_3$ | Yield | m.p. °C. |
|---|---|---|---|---|
| 7 | CH$_3$ (R) | piperidino | 51% | 160° |
| 8 | C$_6$H$_5$ (R) | piperidino | 38% | 194° |
| 9 | CH$_2$OH (S) | piperidino | 75% | 97° |
| 10 | CH$_3$ (R) | 4-methylpiperidino | 73% | 160° |
| 11 | CH$_3$ (S) | 4-methylpiperidino | 72% | 150° |
| 12 | CH(CH$_3$)OH (S) | piperidino | 78% | 106° |

EXAMPLE 13

1-[Nα-(Nα-betanaphthylsulphonyl-(S)-alanyl)-p-cyanophenylalanyl]piperidine: (V: Ar=betanaphthyl; R$_1$=CH$_3$; NR$_2$R$_3$=piperidino)

To a solution of 7.5 g (0.027 mole) of N-(betanaphthylsulphonyl)-(S)-alanine (III: R$_1$=CH$_3$, Ar=-betanaphthylsulphonyl) of S configuration in 300 ml of acetonitrile, there are added successively 11.9 g (0.027 mole) of 1-benzotriazolyl-trisoxy(dimethylamino)phosphonium hexafluorophosphate (BOP), 6.9 g (0.027 mole) of 1-(p-cyanophenylalanyl)piperidine, (II: NR$_2$R$_3$=piperidino), 2.75 g (0.027 mole) of triethylamine. The reactional medium is left under an inert atmosphere, under good agitation, at ambient temperature, for 20 hours. The reactional medium is diluted with ethyl acetate and washed successively with a saturated aqueous solution of sodium chloride, a 2N solution of hydrochloric acid, water, and with a saturated aqueous solution of sodium bicarbonate, then with water. The organic phase is dried on anhydrous sodium sulphate and evaporated to dryness. The residue is purified by chromatography on a silica column (elution: toluene-ethyl acetate, 1:1). White crystals are recovered which are dried.

White crystals, yield: 45%; m.p. 155° C.

EXAMPLE 14

1-[Nα-(Nα-betanaphthylsulphonyl-(RS)-phenylglycyl)-p-cyanophenylalanyl]piperidine: (V: Ar=betanaphthyl; R$_1$=C$_6$H$_5$; NR$_2$R$_3$=piperidino)

Under an inert atmosphere, 3.4 g (0.01 mole) of N-betanaphthylsulphonylphenylglycine (III: R$_1$=C$_6$H$_5$; Ar=betanaphthyl) racemic (RS) in 30 ml of thionyl chloride is taken to reflux for one hour. The reactional medium is evaporated to dryness and the oily residue is dissolved in 50 ml of dichloromethane. The solution of acid chloride (IV:R$_1$=C$_6$H$_5$, Ar=betanaphthyl: R=Cl) in dichloromethane is added drop by drop under an inert atmosphere to a solution of 1.3 g (0.005 mole) of 1-(p-cyanophenylalanyl)piperidine (II: NR$_2$R$_3$=piperidino) and of 0.6 g (0.005 mole) of triethylamine in 20 ml of dichloromethane, which has previously been cooled to between 0° and +5° C. The reactional medium is left at ambient temperature for 20 hours. The insoluble salts are filtered off and the filtrate is evaporated to dryness. The residue is taken up 1N hydrochloric acid and the aqueous acid phase obtained is extracted with dichloromethane. The organic extracts are dried on anhydrous sodium sulphate and evaporated to dryness. The residue obtained after evaporation is purified by chromatography on a silica column (elution: toluene-ethyl acetate 1:1). White crystals are obtained.

White crystals, yield: 80%; m.p.=190° C.

EXAMPLE 15

1-[Nα-(Nα-betanaphthylsulphonyl-(RS)-valyl)-p-cyanophenylalanyl]piperidine (V: Ar=betanaphthyl; R$_1$=CH(CH$_3$)$_2$; NR$_1$R$_2$=piperidino)

To a suspension of 7 g (0.023 mole) of N-betanaphthylsulphonylvaline (III: R$_1$=CH(CH$_3$)$_2$; Ar=-betanaphthyl) racemic (RS) in 10 ml of dichloromethane, kept at between 0° and +5° C., 2.6 g (0.023 mole) triethylamine is added, then 3.4 g (0.025 mole) of isobutyl chloroformate is added drop by drop, and the whole is left for one hour at this temperature. Then 6.2 g (0.024 mole) of 1-(p-cyanophenylalanyl)piperidine (II: NR$_2$R$_3$=piperidino) dissolved in 50 ml of dichloromethane is added, and the reactional medium is left for 20 hours at ambient temperature. After evaporating to dryness, the residue is taken up with water. The aqueous phase is extracted with dichloromethane. The organic extracts are dried on anhydrous sodium sulphate and evaporated to dryness. The oily residue is purified by chromatography on a silica column (elution: toluene-ethyl acetate, 1:1).

White crystals, yield: 78%; m.p. 178° C.

EXAMPLE 16

1-[Nα-(Nα-betanaphthylsulphonyl-(R)-phenylglycyl)-p-amidinophenylalanyl]piperidine: (I: Ar=betanaphthyl; R$_1$=C$_6$H$_5$; NR$_2$R$_3$=piperidino) derivative No. 1

(a) Formation of the imido-ester.

Under an inert atmosphere, 100 ml of methanol is saturated with hydrogen chloride gas at 0° C., and 8.1 g (0.0139 mole) of 1-[N-(N-betanaphthylsulphonyl-(R)-phenylglycyl)-p-cyanophenylalanyl]piperidine (example 8) is added all at once, and the whole is left at 0° C. for 20 hours. After evaporating to dryness without heating the methanol, a white resin is obtained, consisting of the hydrochloride of the imido-ester with the general formula (VII: Ar=betanaphthyl; $R_1=C_6H_5$; $NR_2R_3$=piperidino), which is used without further purification in the last stage.

(b) Formation of the amidine

Under an inert atmosphere, 100 ml of methanol is saturated with ammonia gas at temperatures between 0° C. and +5° C., and the white resin obtained in example 10a, after being dissolved in 20 ml of methanol, is added to this methanol ammonia solution. The reactional mixture is taken to reflux under an inert atmosphere, for 3 hours. After evaporating to dryness, the residue is taken up with an excess of 1N hydrochloric acid. The aqueous acid phase is extracted with dichloromethane. The organic phase is dried on anhydrous sodium sulphate and evaporated to dryness. The semi-crystalline residue, obtained after evaporation, is taken up with water. The insoluble crystals in the water are recovered, dried, then treated with ethyl acetate, and taken to reflux for 10 minutes. The insoluble crystals in the boiling ethyl acetate are filtered off and dried.

White crystals, hydrated hydrochloride, yield: 84%; m.p. 188° C.

The examples 17 to 23 use the same operational methods as those described in example 16. They lead to the Nα-arylsulphonylaminoacyl-p-amidinophenylalaninamides with the general formula (I) and result from the conversion of the nitriles with the general formula (V) by the intermediary of the imido-esters with the general formula (VI). They are tabulated in the following table.

| example | Derivative | Ar | $R_1$ (configuration of the amino acid) | $NR_2R_3$ | x | YIELD | m.p. °C. |
|---|---|---|---|---|---|---|---|
| 17 | 2 | β-naphthyl | $CH_2-C_6H_5(R)$ | piperidino | 1 | 83% | 178° |
| 18 | 3 | β-naphthyl | $CH_3(R)$ | piperidino | 1,5 | 53% | 170° |
| 19 | 4 | β-naphthyl | $CH_3(S)$ | piperidino | 1 | 54% | 176° |
| 20 | 5 | β-naphthyl | $CH_3(R)$ | 4-methylpiperidino | 2 | 69% | 177° |
| 21 | 6 | β-naphthyl | $CH_3(S)$ | 4-methylpiperidino | 2 | 64% | 176° |
| 22 | 7 | β-naphthyl | $CH_2OH(S)$ | piperidino | 1 | 51% | 162° |
| 23 | 8 | β-naphthyl | $CH(CH_3)CH(S)$ | piperidino | 0,5 | 68% | 184° |

The results of the toxicological and pharmacological studies which are reported below have made apparent the useful properties of the invention compounds. These are endowed with a very good thrombin-inhibiting activity, and possess, in addition, remarkable antithrombotic properties in vivo, which compounds with the formulae (A) and (B) and the compound (C) do not show. Compared with heparin, they have a much greater duration of action without inducing an increase in the bleeding time. The subject of the invention is therefore also a medicament presenting, in particular, anti-thrombotic properties, characterized in that it contains, as active principle, a compound with the formula (I) or an addition salt with a therapeutically acceptable mineral or organic acid.

Toxicological study

The invention compounds enjoy a good tolerance and a weak toxicity. Tests carried out on different animal species on the acute, sub-chronic and chronic toxicity have not brought to light any sort of local or general reaction, perturbation or anomaly in the biochemical, macro-scopical and microscopical examinations carried out throughout the tests.

Pharmacological study

In this study, the invention compounds have been compared with heparin and with [N-(N-betanaphthylsulphonylglycyl)-p-amidinophenylalanyl]piperidine, a compound of closely similar structure described as a powerful thrombin inhibitor (J. HAUPTMANN & COLL., THROMB., RES., 38 771-775, 1983) and which will be called derivative C.

(1) Thrombin time.

The coagulation time of citrated plasma in the presence of thrombin is measured ex vivo in the rat, according to the technique of BIGGS R. M., (Human blood coagulation, haemostasis and thrombosis: Oxford, Blackwell Scientific Publications, 1972).

The samples were taken one hour after sub-cutaneous administration of the compound under test, by puncture of the abdominal aorta. The blood was collected on sodium citrate at 3.8% (1 volume for 9 volumes of blood). The plasma was obtained by centrifuging at 2600 g for 10 minutes. To 0.2 ml of the plasma, 0.2 ml of a thrombine solution was added, (20 U/ml). The coagulation time was recorded. The results are assembled in the following table and expressed in seconds.

| Product | Dose mg/Kg | Route | Result (time in secs.) | % extension | p |
|---|---|---|---|---|---|
| control | | s.c. | 6 ± 0 | | |
| heparin | 10 | s.c. | 20 ± 4 | 230 | 0.001 |
| control | | s.c. | 7 ± 0 | | |
| derivative C | 10 | s.c. | 9 ± 0 | 29 | 0.001 |
| control | | s.c. | 5.9 ± 0 | | |
| derivative No. 7 | 10 | s.c. | 48.6 ± 10.8 | 782 | 0.001 |
| control | | s.c. | 8.2 ± 0.2 | | |
| derivative No. 4 | 10 | s.c. | 49.9 ± 6.2 | 508 | 0.001 |
| control | | s.c. | 7.7 ± 0.1 | | |
| derivative No. 6 | 10 | s.c. | 12.7 ± 0.3 | 65 | 0.001 |
| control | | s.c. | 7 ± 0 | | |
| derivative No. 8 | 10 | s.c. | 87 ± 11 | 1104 | 0.01 |

(2) Venous thrombosis with the spiral

The tests were carried out according to an adaptation of the method of T. KUMADA et al., (Thromb. Res., 18, 189-203, 1980) A metallic spiral (re-cut dentist's paste rammer) is inserted in the inferior vena cava of an anesthetized rat. The animals had received the compound under test one hour earlier by sub-cutaneous route. Five hours later, the spiral was withdrawn with the thrombus which it retained, and was then dried by repeated dabbing with filter paper and weighed. The spiral was then relieved of the thrombus, dried and weighed again. The weight difference gives the weight of the thrombus. The results are assembled in the following table.

| Product | Dose mg/Kg | Weight of thrombus in mg | Variation | p |
|---|---|---|---|---|
| control | | 4.47 ± 0.51 | | |
| heparin | 5 | 2.91 ± 0.53 | −35% | 0.05 |
| heparin | 10 | 1.62 ± 0.34 | −64% | 0.001 |
| heparin | 20 | 0.26 ± 0.04 | −94% | 0.001 |
| control | | 4.77 ± 0.47 | | |
| derivative C | 20 | 3.99 ± 0.45 | −15% | n.s. |
| derivative C | 50 | 3.63 ± 0.37 | −24% | n.s. |
| derivative C | 100 | 3.08 ± 0.28 | −35% | 0.01 |
| control | | 3.81 ± 0.38 | | |
| derivative No. 4 | 5 | 2.67 ± 0.22 | −30% | 0.05 |
| derivative No. 4 | 10 | 2.48 ± 0.35 | −35% | 0.05 |
| derivative No. 4 | 20 | 1.92 ± 0.14 | −50% | 0.001 |
| control | | 3.72 ± 0.33 | | |
| derivative No. 4 | 50 | 2.62 ± 0.26 | −30% | 0.05 |
| control | | 3.72 ± 0.33 | | |
| derivative No. 7 | 10 | 2.42 ± 0.26 | −35% | 0.01 |
| control | | 4.28 ± 0.53 | | |
| derivative No. 8 | 10 | 2.07 ± 0.12 | −52% | 0.01 |

(3) Bleeding time

This study was carried out according to an adaptation of the technique of L. STELLA et al., (Thromb. Res.; 1975 7, 709-716). After anesthetizing a rat with pentobarbital, its tail was cut at 5 mm from the end and the blood from the wound was carefully dabbed every 15 seconds with a filter paper until haemostasia occurred. The latter was obtained when no stain appeared during one minute. The products to be tested are administered by sub-cutaneous route one hour before the tail was cut. The results are assembled in the following table:

| Product | Dose mg/Kg | Duration in seconds | limits | p |
|---|---|---|---|---|
| control | | 360 | 330-480 | |
| heparin | 5 | 465 | 330-540 | n.s. |
| heparin | 10 | 3600 | 525->3600 | 0.01 |
| heparin | 20 | 3600 | 690->3600 | 0.01 |
| control | | 540 | 450-675 | |
| derivative C | 10 | 375 | 360-510 | n.s. |
| derivative C | 20 | 750 | 420-960 | n.s. |
| derivative C | 50 | 600 | 435-615 | n.s. |
| control | | 405 | 390-510 | |
| derivative No. 4 | 10 | 440 | 400-520 | n.s. |
| derivative No. 4 | 20 | 450 | 420-530 | n.s. |
| derivative No. 4 | 50 | 480 | 420-3500 | n.s. |
| control | | 540 | 400-680 | |
| derivative No. 6 | 10 | 380 | 340-480 | n.s. |
| derivative No. 6 | 20 | 550 | 420-700 | n.s. |
| derivative No. 6 | 50 | 600 | 430-605 | n.s. |
| control | | 525 | 450-610 | |
| derivative No. 7 | 10 | 605 | 530-760 | n.s. |
| derivative No. 7 | 20 | 585 | 495-860 | n.s. |
| derivative No. 7 | 50 | 540 | 460-650 | n.s. |

Bleeding time: this study has clearly shown the risk of hemorrhage induced by heparin which extends considerably the bleeding time. Being without action on the bleeding time, the invention derivatives possess a much greater safety margin than heparin does.

The medicament of the invention can be presented for oral administration in the form of tablets, sugar-coated tablets, capsules, drops, syrup or granules. It can also be presented for rectal administration in the form of suppositories and for parenteral administration in the form of an injectable soluteion. Each unit dose advantageously contains from 0.005 g to 0.500 g of active principle as a function of the age of the invalid and of the seriousness of the affection treated. By way of non-limitative examples, there are given below several pharmaceutical formulations of the invention medicament.

| (1) tablets | |
|---|---|
| derivative No. 4 | 0.050 g |
| excipient | lactose, corn starch, talc, colloidal silica, magnesium stearate. |
| (2) sugar-coated tablets | |
| derivative No. 6 | 0.025 g |
| excipient | sugar, corn starch, polyvinyl pyrrolidone, silicic acid, magnesium stearate, talc, "orange yellow". |
| (3) capsules | |
| derivative No. 3 | 0.100 g |
| excipient | talc, wheat starch, magnesium stearate |
| (4) suppositories | |
| derivative No. 5 | 0.050 g |
| excipient | semi-synthetic glycerides |
| (5) injectable solution | |
| derivative No. 11 | 0.025 g |
| excipient | isotonic solvent, q.s. for 5 ml. |

For its anti-coagulant and anti-thrombotic properties, without secondary effects due to the risk of hemorrhagia, the invention medicament is usefully administered in the prevention and treatment of thromboembolic disease.

We claim:

1. Compounds with the formula

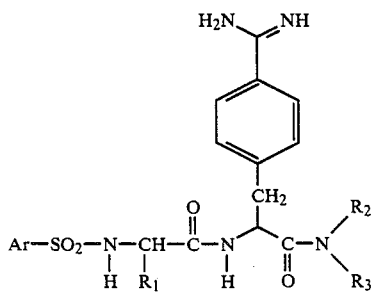

in which:

$R_1$ represents a lower alkyl, lower hydroxyalkyl or benzyl group, a phenyl group or a 4-hydroxyphenyl group, $R_2$ and $R_3$, identical or different, each represents a lower alkyl or hydroxyalkyl, lower alkenyl, or lower alkynyl radical, or together with the nitrogen to which they are attached, form a saturated heterocycle selected from the group consisting of morpholino, thiomorpholino, pyrrolidino unsubstituted or substituted by an alkoxycarbonyl or carboxyl group, piperazino, 4-(lower alkyl)piperazino, 4-(lower hydroxyalkyl)piperazino, or piperidino unsubstituted or substituted by a lower alkyl, benzyl, hydroxy, lower hydroxyalkyl, amino, lower aminoalkyl, alkoxycarbonyl or carboxyl group;

Ar represents a phenyl group, an alphanaphthyl or betanaphthyl group which may be substituted or unsubstituted, a heteroaryl group chosen from pyridyl, quinolinyl, isoquinolinyl, possibly substituted, and their addition salts with pharmaceutically acceptable mineral or organic acids as well as the isomers or their mixtures.

2. Compound of claim 1 with the formula (I) in which $R_1$ represents an alkyl or hydroxyalkyl radical.

3. Compounds of claim 1 with the formula (I) in which the group

represents a substituted or unsubstituted piperidino radical.

4. Compounds of claim 1 with the formula (I) in which Ar represents a substituted or unsubstituted naphthyl radical.

5. 1-[Nα-(Nα-betanaphthylsulphonyl-(S)-alanyl)-p-amidinophenylalanyl]piperidine and its pharmaceutically acceptable salts.

6. 1-[Nα-(Nα-betanaphthylsulphonyl-(S)-alanyl)-p-amidinophenylalanyl]-4-methyl-piperidine and its pharmaceutically aceptable salts.

7. 1-[Nα-(Nα-betanaphthylsulphonyl-(S)-seryl)-p-amidinophenylalanyl]piperidine and its pharmaceutically acceptable salts.

8. 1-[Nα-(Nα-betanaphthylsulphonyl-(S)-threonyl)-p-amidinophenylalanyl]piperidine and its pharmaceutically acceptable salts.

9. An antithrombotic composition comprising, as active principle, an effective amount of a derivative selected from the group consisting of a compound with the formula (I) according to claim 1 and one of its pharmaceutically acceptable salts in admixture with a pharmaceutically acceptable diluent.

10. The composition according to claim 9, characterized in that each unit dose contains from 0.005 g to 0.500 g of active principle.

11. Compounds according to claim 1 with the formula (I) in which $R_1$ represents an alkyl or hydroxyalkyl radical, $NR_2R_3$ represents a substituted or unsubstituted piperidino radical and Ar represents a substituted or unsubstituted naphthyl radical.

* * * * *